United States Patent [19]

Beachey

[11] Patent Number: 4,597,967

[45] Date of Patent: Jul. 1, 1986

[54] SYNTHETIC POLYPEPTIDE FRAGMENTS

[75] Inventor: Edwin H. Beachey, Memphis, Tenn.

[73] Assignee: The University of Tennessee Research Corp., Knoxville, Tenn.

[21] Appl. No.: 700,625

[22] Filed: Feb. 12, 1985

Related U.S. Application Data

[60] Division of Ser. No. 503,273, Jun. 10, 1983, Pat. No. 4,521,334, and a continuation-in-part of Ser. No. 402,355, Jul. 27, 1982.

[51] Int. Cl.[4] .................. A61K 39/00; A61K 39/385; C07K 7/10
[52] U.S. Cl. ...................................... 424/88; 514/12; 530/324; 530/806; 530/405; 530/815
[58] Field of Search .................. 424/88; 260/112.5 R; 514/12

[56] References Cited

PUBLICATIONS

J. Exp. Med., vol. 151, (1980) 695–708.
The Journal of Exp. Med., vol. 134, (1971) 351–365.
The Journal of Exp. Med., vol. 151 (1980) 1026–1038.
The J. of Exp. Med., vol. 145, (1977) 1469–1483.
Nature, 292, (1981) 457–459.
J. Biol. Chem., 2551 (1980) 6284–6289.
Proc. Nat'l. Acad. Sci. 75, (1978) 3163–67.
Biochem. & Biophys. Res. Commun. 92, (1980) 546–553.
J. Immun. 126, (1981) 1499–1505.
Streptococcal Disease, pp. 149–160 (1981).
J. Exp. Med., 150, (1979) 862–877.
Hosp. Prac., (1979) 49–57.
Immunogenicity in Animals and Man of a Structurally Defined Polypeptide of Streptococcal M Protein, vol. XCii, (1979) 346–354.
Separation of the Type Specific M Protein from Toxic Cross Reactive Antigens of Group A Streptococci, vol. XC, (1977) 390–400.
The J. Experimental Med., vol. 143, (1976) 759–771.
Biochem. and Biophys. Research Commun., pp. 546–553, vol. 92, (1980).
Biological Absts., vol. 50, p. 20360.
Toxins, 307–312.
Infection and Immun., (1984), pp. 122–126, vol. 43, No. 1.
The J. of Biol. Chem., 258, (1983) 13250–13257.
Nature, vol. 232, (1971) 478–480.
Nature, vol. 292, (1981) 457–459.
Proc. Nat'l. Acad. Sci. 76, 1425–1429 (1979).
Biochemistry (1975) 423–438.
Biochem., vol. 10, (1971) 4912–21.
Biochemistry, vol. 14 (1975) 1933–38.
European J. Biochem. (1967) 80–91, vol. 1.
Biochem., vol. 11 (1972) 1828–1835.
Amino Acid Seg. of Chick Skin Collagen, vol. 9, (1970) 796–804.
Biochemistry, vol. 16, No. 6, (1977) 1158–1163.
Infection and Immunity (1974) 244–248 vol. 9.
The J. of Clinical, vol. 52, (1973) 2563–2570.
Immunochemistry of Group A Streptococcal M Proteins, vol. 4, pp. 401–410.
Proc. Nat'l. Acad. Sci. 78, 4689–4693 (1981).
Biochemistry, vol. 13, (1974) 235–245.
Proc. Nat'l. Acad. Sci. 78, (1981) 3824–3828.
J. of Experimental Med., vol. 146 (1977) 579–599.

*Primary Examiner*—Delbert R. Phillips
*Attorney, Agent, or Firm*—Weiser & Stapler

[57] ABSTRACT

Peptide fragments of streptococcal M protein named CB3, CB4, and CB5 and related synthetic peptides have been identified. When linked to a protein carrier which is polylysine the conjugates of CB3, CB4, CB5, and S-CB3 are capable of evoking type specific opsonic antibodies against streptococci.

56 Claims, 6 Drawing Figures

FIG. 5 Double Immunodiffusion in Agar Gel of S-CB3 Immune Rabbit Serum Against Polylysine Conjugates of CB3 (p-CB3), CB4 (pCB4), CB5 (pCB5), S-CB3 (pS-CB3), S-CB7 (pS-CB7) and pep M24

SYNTHETIC POLYPEPTIDE FRAGMENTS

This application is a division, of application Ser. No. 503,273, filed June 10, 1983, now U.S. Pat. No. 4,521,334, and a continuation in part of U.S. application Ser. No. 402,355 entitled Synthetic Peptides Corresponding to Antigenic Determinants of the M Protein of *Streptococcus pyogenes*, filed July 27, 1982, whose inventor is Edwin H. Beachey.

This invention relates to peptide fragments of the M protein of *S. pyogenes*. More particularly, the invention relates to the subpeptides which are derived by cleavage of a peptic extract of type 24M protein with cyanogen bromide and which are able to inhibit opsonic antibodies obtained from rabbits immunized with the uncleaved pep M24 molecules.

The invention further relates to haptens which, when linked to a suitable carrier, elicit high titers of type specific opsonic and bactericidal antibodies in rabbits.

The invention further relates to the conjugates of these haptens with appropriate carriers which evoke immune responses which are type specific for type 24 streptococci, and which are not serologically crossreactive with tissue antigens of the human or of the host heart.

The invention further relates to the biologically active compositions which comprise the peptide fragments and a biologically acceptable carrier and which are immunogenic with respect to *Streptococcus pyogenes*.

The invention further relates to the method for controlling streptococcal infections in a mammal which comprises administering the biologically active compositions to said mammal.

The invention further relates to the synthetic peptides which correspond to antigenic determinants of the M protein of *S. pyogenes*. More particularly, the invention relates to synthetic immunogenic peptides which are able to elicit opsonic antibodies which are type-specific for type 24 streptococci and which are not serologically cross-reactive with tissue antigens of the human or of the host heart.

Recently Audibert et al. actively immunized laboratory animals against diptheria toxin using a chemically synthesized oligopeptide. Audibert, F. et al., Nature 289, 593–594 (1981). This work does not show, however, that a synthetic peptide antigen can raise antibodies which promote phagocytosis and killing of a bacterial pathogen.

U.S. Pat. No. 4,284,537, to E. Beachey, issued Aug. 18, 1981, disclosed the amino acid sequence of two peptide fragments derived from M protein. It also disclosed that each of these natural fragments, when covalently linked to a carrier such as polylysine, was able to elict type-specific opsonic antibodies effective against *Streptoccocus pyogenes*. Each of these fragments was a natural extract, and each contained 35 amino acids.

The above-referred to patent application teaches and describes inter alia, a synthetic peptide (S-CB7) and that one of the protective determinants is located in a specific fragment of S-CB7 of type 24 M protein which contains only twelve amino acid residues (S18-29CB7). S-CB7, as described, differs from the native CB-7 fragment in that the COOH-terminal residue of S-CB7 is methionine, in contrast to homoserine. The specification also teaches and describes covalently linked conjugates of S-CB7 and appropriate hapten carriers, natural, like BSA or OVA or synthetic, like polylysine. Further details about this work have been published in Nature on July 30, 1981, by Beachey et al. vol. 292, pages 457–459.

Notwithstanding these advances, there remains a serious need, as yet unfilled, to determine precisely the minimal structure of the M protein molecule required to evoke protective immunity without causing tissue cross-reactive adverse reactions. The problem has been described by Hasty et. al. in the J. Exp. Med., Vol. 155, page 1010, April 1982. Another attempt in predicting protein antigenic determinants from amino sequences (including the streptococcal M protein) has been published by Hopp et. al. in the Proc. Natl. Acad. Sci. USA, Vol. 78, No. 6, pps. 3824–28, June 1981. The present invention marks another forward step and provides another advance in the medical sciences, particularly in the control of streptococcal infections.

Accordingly, it is a primary object of the invention to provide small peptide fragments of *S. Pyogenes* which are able to inhibit opsonic antibodies obtained from a mammal which has been immunized with uncleaved pep M24 molecules.

It is also an object of the invention to provide peptide fragments which are useful as haptens which, when linked to a suitable carrier, are able to evoke high titers of type specific opsonic and bactericidal antibodies.

Another object of the invention is the conjugates of these haptens with appropriate carriers which evoke immune responses which are type specific for type 24 streptococci.

Another object of the invention is the production of biologically active compositions which are immunogenic with respect to *S. pyogenes*.

Another object of the invention is to provide for a method of controlling streptococcal infections in a mammal.

Other worthwhile objects will become apparent from the disclosure herein. Other features and advantages of the invention will appear from the examples which follow and by referring to the appended drawings in which.

Figure 1:
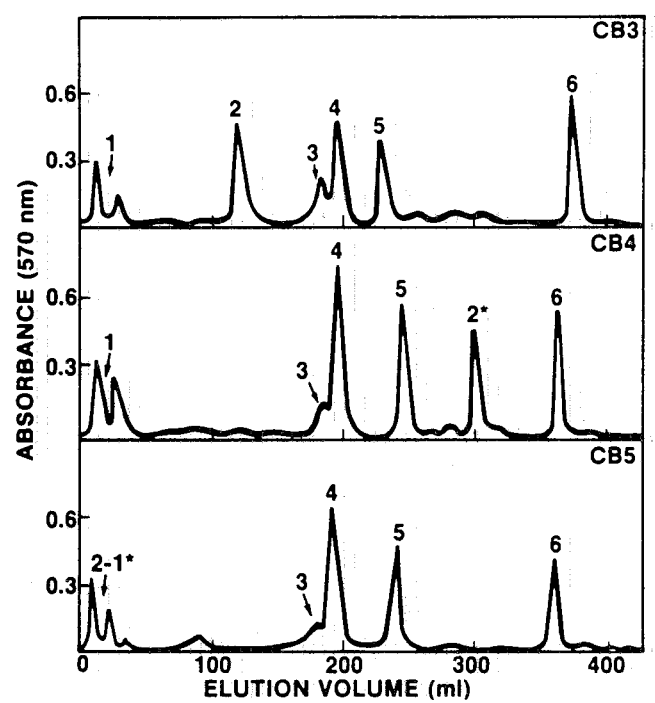
FIG. 1 shows Tryptic Peptides Isolated from CB3, CB4 and CB5 by Ion Exchange Chromatography on PA35 Resin.

The mechanism whereby streptococcal infections give rise to complications such as rheumatic fever have remained to a large extent unexplained to date. Because the sera of some patients with rheumatic fever show serological cross-reactivity between heart tissue antigens and certain streptococcal antigens, it has been feared that immunization with intact M-protein vaccines may lead to rheumatic heart disease. See, for instance, Stollerman, *Rheumatic Fever and Streptococcal Infection* (Greene and Stratton, New York, 1975). It has been observed that rabbits and mice immunized with cyanogen bromide fragments (CB6 or CB7) of type 24 M protein containing only 35 amino acid residues each developed opsonic and protective antibodies against type 24 streptococci.

The immunogenicity of small peptide fragments is encouraging for the development of safe and effective vaccines against those streptococcal infections that initiate rheumatic fever and rheumatic heart disease. The efficacy of very small peptides would permit disposal of a large portion of the M protein molecule and, therefore, should reduce the chances of eliciting immunological cross-reactions against host tissues. Thus, the continued identification of peptide structures responsible for protective immunity should yield a pool of small peptides that may eventually be synthesized and administered safely to humans as vaccine broadly protective against many serotypes of streptococci, particularly against those strains that trigger post-streptococcal sequelae.

The protective antigenic determinants of type 24 group A streptococci appear to reside in repeating covalent structures of the M protein molecule. Each of seven distinct subpeptides derived by cleavage of a peptic extract of type 24 M protein (pep M24) with cyanogen bromide (CNBr) inhibit opsonic antibodies obtained from rabbits immunized with the uncleaved pep M24 molecule. The $NH_2$-terminal sequences of two of these fragments, CB1 and CB2, are identical with each other and with the $NH_2$-terminal sequence of the uncleaved pep M24 through at least the first 23 residues. The sequences of the remaining five peptides were entirely different from CB1 and CB2, but were identical with each other through the first 20 residues; thereafter, the sequences showed slight variability (Beachey, E. H. et al., Proc. Natl. Acad. Sci. U.S.A. 75, 3163–3167 (1978) hereinafter referred to as 1. All references listed by numbers are tabulated at the end of the specification and are herein incorporated as reference.).

When covalently linked to polylysine and emulsified in complete Freund's adjuvant, the subpeptides CB1, CB6 and CB7 have been shown to evoke type specific protective immune responses in laboratory animals (2). The complete covalent structures of CB6 and CB7 and their alignment with each other and with part of a third repeating peptide have been established. CB6 and CB7 each contain 35 amino acid residues and their sequences are identical to each other except for three substitutions at positions 21, 24 and 26 (2, U.S. Pat. No. 4,284,537, issued Aug. 18, 1981). Recently, a chemically synthesized peptide (S-CB7) identical to native CB7 except that the COOH-terminal residue of S-CB7 was methionine not homoserine was shown to evoke protective immune responses against challenge infections of mice with type 24 streptococci. (3, U.S. patent application Ser. No. 402,355).

In accordance with the invention, the covalent structures and immunogenicity of CB3, CB4, CB5, have been determined. In addition, a chemically synthesized analogue of CB3 (S-CB3) has been prepared and its immunogenicity has been determined.

CB3 and CB4 each contain 35 amino acid residues whereas CB5 contains 37 residues. The homologies among these three peptides and with CB6 and CB7 are remarkable in that the five peptides are identical to each other except for as few as one to six amino acid substitutions. In addition, the chemically synthesized peptide (S-CB3) resembles native CB3 except that the COOH-terminal residue is methionine instead of homoserine possessing similar protective immunogenicity. Data obtained with a set of monoclonal antibodies demonstrate that the repeating covalent structures of the M protein molecule contain several unique and several repeating, protective and nonprotective epitopes whose antigenic specificity is determined by as few as a single amino acid substitution within the 35-residue repeating peptide.

The complete amino acid sequences of three cyanogen bromide peptide fragments (CB3, CB4, and CB5) of type 24M protein extracted from *Streptococcus Pyogenes* organisms by limited pepsin digestion (pep M24) were determined by automated Edman degradation of the uncleaved peptides and their tryptic peptides.

Cyanogen bromide cleavage of a peptide results in cleavage of the peptide at the position of methionine. The resultant peptide fragments have a homoserine moiety in place of methionine.

The resultant fragment is structurally different from the original larger peptide. However, since the starting material of the fragments is native M protein, and not a stepwise synthesis from individual amino acids, they are hereinafter referred to as "native" fragments.

CB3 and CB4 each contain 35 amino acid residues whereas CB5 contains 37.

The sequence of CB3 was found to be:
Asn-Phe-Ser-Thr-Ala-Asp-Ser-Ala-Lys-Ile-Lys-Thr-Leu-Glu-Ala-Glu-Lys-Ala-Ala-Leu-Glu-Ala-Glu-Lys-Ala-Asp-Leu-Glu-Lys-Ala-Leu-Glu-Gly-Ala-Hse.

The sequence of CB4 was found to be:
Asn-Phe-Ser-Thr-Ala-Asp-Ser-Ala-Lys-Ile-Lys-Thr-Leu-Glu-Ala-Glu-Lys-Ala-Ala-Leu-Glu-Ala-Arg-Gln-Ala-Asp-Leu-Glu-Lys-Ala-Leu-Glu-Gly-Ala-Hse.

The sequence of CB5 was found to be:
Asn-Phe-Ser-Thr-Ala-Asp-Ser-Ala-Lys-Ile-Lys-Thr-Leu-Glu-Ala-Glu-Lys-Ala-Ala-Leu-Glu-Ala-Arg-Lys-Ala-Asp-Leu-Asp-Asp-Ala-Leu-Glu-Leu-Glu-Gly-Ala-Hse.

A comparison of the structures of these three peptide fragments with those previously reported for CB6 and CB7 revealed as few as one to six amino acid substitution among the five repeating peptides. CB4 and CB6 differed by a single Asp/Glu substitution at position 26.

A chemically synthesized peptide (S-CB3) identical to native CB3 except that S-CB3 contained methionine instead of homoserine at its COOH-terminus was similarly immunogenic.

Chemically synthesized peptides S-CB4 and S-CB5 are also within the scope of the invention. These peptides are similar to their respective native peptides CB4 and CB5 except that the chemically synthesized peptides S-CB4 and S-CB5 contain methionine instead of homoserine at their COOH-termini.

The invention also provides a polypeptide which comprises an amino sequence of fragments CB3, CB4, CB5, CB6, or CB7 wherein one or more of the amino acids in the sequence of these fragments is interchangeable with (or is substitutable by) one or more amino acid in the corresponding (numerical) position in one of the other amino acid fragments. More preferably, this applies to the fragments CB3, CB4, and CB5. Thus, for illustrative purposes in CB3, Glu (residue 23) may be replaced by Arg; Leu in CB5 may be replaced by Gly; or Glu in CB6 may be replaced by Lys. For illustrative purposes, the more readily interchangeable amino acids are shown in "boxes" in FIG. 2 hereinafter.

Likewise, it will be noted the same equivalence and substitution can be done with the corresponding synthetic amino acid sequence, namely, those Met-terminated, rather than Hse-terminated.

Figure 2:
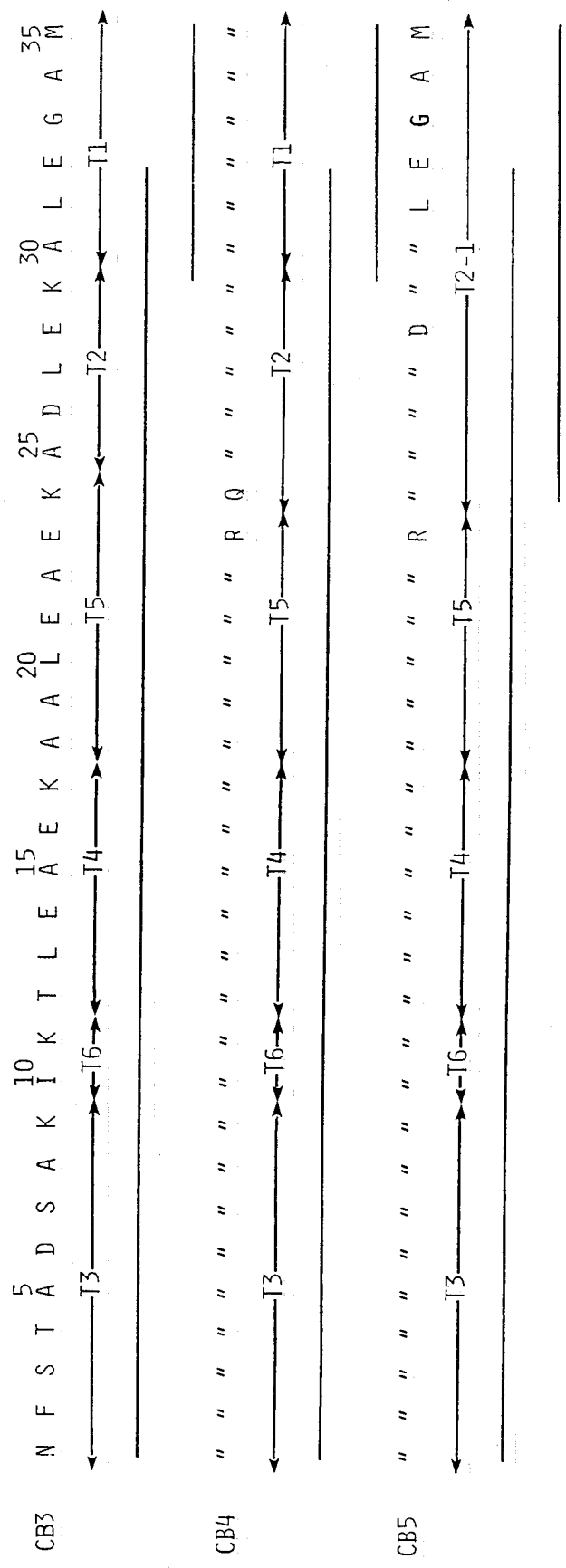
FIG. 2 shows comparisons of the complete amino acid sequence of CB3, CB4 and CB5.
Figure 3:
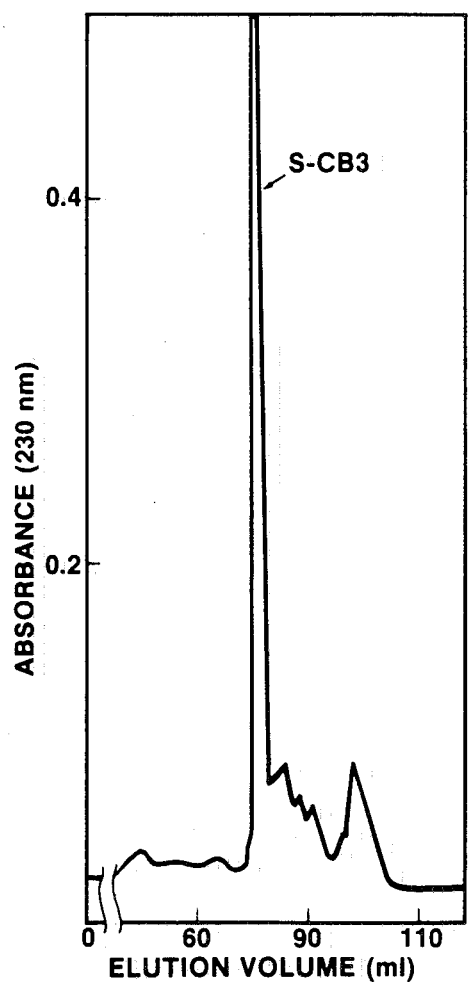
FIG. 3 shows reverse-phase HPLC purification of chemically synthesized peptide fragment S-CB3.

It is also within the contemplation of the invention that one or more amino acids which are not shown in the "boxes" in FIG. 2 is substitutable (or replaceable) by another amino acid of those of Table II whether or not that amino acid is shown in a box or not.

What characterize or identifies the polypeptides of the invention (whether the Met or Hse-terminated ones are those which are effective to elicit type specific opsonic antibodies to *Streptococcus pyrogenes* without causing tissue, especially heart cross-reactive, antibodies against a rheumatogenic strain of *S. pyogenes.* Generally, this property is most evident when the peptide is linked to a suitable carrier.

A typical amino acid sequence of the invention comprises an amino acid sequence of a maximum of 35 to 37 amino acids which length contains the antigenic determinant having the activity defined above and which comprises, preferably, selections from the amino acids shown in FIG. 2.

A preferred amino acid sequence is the following:

Asn-Phe-Ser-Thr-Ala-Asp-Ser-Ala-Lys-Ile-Lys-Thr-Leu-Glu-Ala-Glu-Lys-Ala-Ala-Leu-A-Ala-B-C-Ala-D-Leu-E-F-Ala-Leu-Glu-G-H-I wherein A is Glu or Ala
B is Glu or Arg
C is Lys or Gln
D is Asp or Glu
E is Glu or Asp
F is Lys or Asp
G if Gly or Leu
H is Ala or Glu
I is Hse, Met, Gly-Ala-Hse, or Gly-Ala-Met.

Mapping studies with monoclonal antibodies revealed a number of distinct protective and nonprotective epitopes. The single Asp/Glu substitution between CB4 and CB6 rendered the 35-residue peptide unrecognizable by protective monoclonal antibodies but recognizable by a nonprotective one. These studies demonstrate that the repeating covalent structures of native and chemically synthesized polypeptide fragments of streptococcal M protein possess several unique as well as repeating epitopes that evoke opsonic and hence protective, but not heart cross-reactive, antibodies against a rheumatogenic strain of *S. pyogenes.*

The type 24 M protein polypeptide (pep M24) was extracted by limited digestion of whole *S. pyogenes* cells with pepsin and purified by ammonium sulfate fractionation and ion exchange chromatography described in Example 1. Digestion of pure pep M24 with CNBr, as described in Example 2, yielded seven distinct peptides which were separated by a combination of Sephadex G-50SF molecular sieve and CM-cellulose chromatography. The two 35-residue peptides, CB3 and CB4 and the 37 residue peptide CB5 were analyzed further by trypsin digestion and automated Edman degradation, as described in Example 3. Six tryptic peptides were isolated from CB3 and CB4 but only five from CB5 by ion exchange chromatography on PA35 resin (FIG. 1). Peptide T1 of both CB3 and CB4 and peptide T2-1 of CB5 contained homoserine and therefore represented the COOH-terminal peptide. The amino acid composition and summation of the trypic peptides accounted for all the CB5, respectively (Table I). Tryptic peptide T2-1 of CB5 containing 14 amino acid residues was the largest peptide and from comparisons of its amino acid composition with that of peptides T1 and T2 of CB3 and CB4 as well as that of CB6 and CB7 (2), we deduced its COOH-terminal location in CB5.

Each of the tryptic peptides of the respective CNBr peptides were analyzed by sequential Edman degradation as described in Example 5 and their amino acid sequences were compared to the sequential degradations of intact CB3, CB4, and CB5, respectively. In this way the alignment of the tryptic peptides was established. The complete sequences are depicted in FIG. 2. The sequence of CB4 is identical to that of CB3 except for two amino acid substitutions of arginine and glutamine at positions 23 and 24, respectively. CB5 is identical to CB4 through the first 35 residues except for substitutions of lysine, aspartic acid, leucine, glutamic acid and glycine at positions 24, 28, 29, 33, 34, and 35, respectively. CB5 contains two additional amino acids, alanine and homoserine at positions 36 and 37, respectively. A comparison of the variable regions (from residue 21 to the COOH-terminal residue) of these three CNBr peptides with those of CB6 and CB7 reported previously (2) reveals a minimum of one and a maximum of six amino acid substitutions through residue 35 (Table II). Thus, CB5 and CB6 differ from each other at six positions whereas CB4 and CB6 differ only at one position.

The CB3 polypeptide fragment of pep M24 was chemically synthesized and purified by reverse-phase HPLC on a column of Ultrasphere ODS2 beads, Example 4, (FIG. 3). Amino acid analysis and automated Edman degradation of the purified synthetic peptide to the penultimate residue gave the amino acid sequence of S-CB3 as identical to that of the native CB3 except that the COOH-terminal residue of S-CB3 was methionine, not homoserine.

It has been previously shown that each of the seven CNBr peptide fragments of pep M24 protein was capable of inhibiting type 24 opsonic antibodies (1). Furthermore, the native CB6, CB7, and CB1, as well as a chemically synthesized peptide S-CB7, when covalently linked to polylysine, are capable of evoking opsonic antibodies against type 24 streptococci (2, 3). Having established the complete covalent structures of CB3, CB4, and CB5, it was of interest to determine if these peptides were capable of raising opsonic and protective antibodies as well. Minimal structural differences among the peptides in a region predicted to possess a highly immunogenic determinant (20) may shed light on the conformational constraints governing protective immunodeterminants.

Therefore, the invention further provides that the obtained sequences of amino acids can be conjugated with a carrier (natural or synthetic), whereby a conjugate is formed which is able to elicit in vivo the production of antibodies capable of neutralizing immunologically the S. pyogenes. These conjugates are also part of the invention. They are well suited for being administered with an adjuvant, either a natural one such as complete Freund's adjuvant or a synthetic one such as MDP or MDP type.

When conjugated to polylysine and administered in the presence of an immunostimulant, CB3, CB4, and CB5 each are capable of evoking type specific opsonic and bactericidal antibodies against streptococci in rabbits.

Furthermore, none of the conjugated native or synthetic peptides raised antibodies that reacted in immunofluorescence tests with sarcolemmal membranes of human heart tissue.

In accordance with the invention, the carriers which are used to make the conjugate with the peptide sequences of the invention are any "natural" or synthetic carrier. The term carrier is a recognized term in the art and literature and sometimes is referred to as "coupler" or as "protein carrier." Numerous molecules, especially proteins and polysaccharides (in the mouse), may be coupled covalently to a hapten to act as a carrier. For this purpose, haptens may also be bound to erythrocytes, bacteriophages, artificial or synthetic macromolecules, and even to insoluble carriers. The hapten should possess one or several reactive groups that permit binding (covalent bonds) to carrier functional groups, under physicochemical conditions that maintain the integrity of the hapten structure, and as much as possible, of the carrier protein.

In some cases, binding of hapten to carrier requires mere contact (this is the case for nitrophenyl derivatives); most often, however, a coupling agent is required. When the hapten itself does not possess any reactive group, it may be introduced through a previous reaction. Thus, in order to couple steroids without carboxyl function to proteins, their alcohol function may be transformed into hemisuccinate, which introduces a carboxyl group.

Natural carriers used in accordance with the invention are known and are, typically, BSA or OVA. Synthetic carriers are, typically, polylysine. Hapten carriers are well known in the literature and need not be further described here to one skilled in the art. Generally, these carriers are covalently linked to the protein sequence.

Moreover, it has been found that the coupled antigen can be administered with a natural immunostimulant, preferably complete Freund's adjuvant or a synthetic immunostimulant, preferably of the MDP type, like MDP, its analogs and derivatives in aqueous saline solution, such as phosphate buffered saline ("PBS").

It is contemplated in accordance with the invention that whenever the term "MDP" is used for the synthetic immunostimulant, the term is and does include any synthetic immunostimulant which contains (or encompasses, or includes, etc.) the basic MDP (or the nor-MDP, i.e., 2-(2-acetamido-2-deoxy-D-glucos-3-O-yl)-D-propionyl-L-alanyl-D-isoglutamine), structure, which structure has been recognized in the art to be the minimal structure to contribute to immunogenicity. The term "MDP immunostimulant", or "MDP-type" or "nor-MDP type" or MDP analogs and derivatives are to be taken broadly. Such MDP immunostimulants are well known in the literature, which is incorporated by reference and include the following for illustrative purposes: U.S. Pat. Nos. 4,082,735, 4,082,736, 4,153,684, 4,220,637, 4,101,649, 4,186,194, 4,235,771, and the following publications: *Biken Journal*, Vol. 18, 105–111, 1975; *Microbiology* (1977) 388–394; *Cellular Immunology* 21, 243–249 (1976); *Proc. Natl. Acad. Sci. USA*, Vol. 73, No. 7, pps 2472–2475, July 1976; *Int. J. Peptide Protein Res.*, 9, 1977, pps. 249–257; *Biken Journal*, Vol. 20, pps. 95–103, 1977; *C. R. Acad. Sc. Paris*, t. 285 (Sept. 12, 1977); *Prog. Allergy*, Vol. 25, pps. 63–105 (Karger, Basel 1978); and *Cellular Immunology* 35, pps. 173–179 (1978).

When injected with 25 nmol of the unconjugated peptide fragments emulsified in complete Freund's adjuvant, none of the immunized rabbits developed opsonic antibody responses. However, when S-CB3 is injected in higher doses, opsonic antibody responses are developed.

Figure 4:
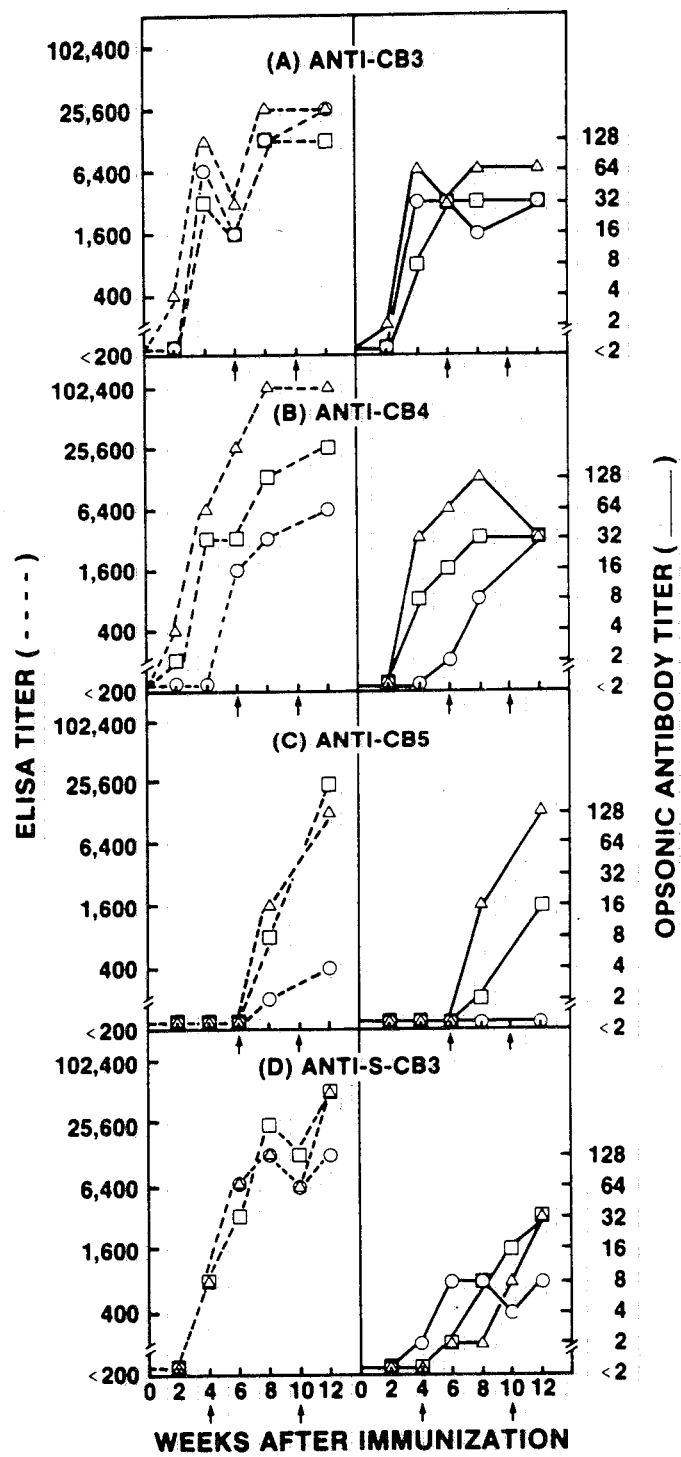
FIG. 4 shows immune responses in rabbits against polylysine conjugated peptide fragments of type 24 streptococcal M protein.
Figure 5:
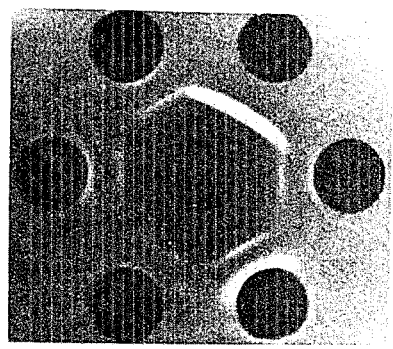
FIG. 5 shows double immunodiffusion in agar gel of S-CB3 immune rabbit serum against polylysine conjugates of CB3 (p-CB3), CB4 (pCB4), CB5 (pCB5), S-CB3 (pS-CB3), S-CB7 (p S-CB7) and pep M24.

When injected with polylysine conjugates of the peptides, each of three rabbits injected with CB3, CB4, CB5, or S-CB3 developed immune responses as determined by ELISA (FIG. 4). All animals except one (one of three rabbits immunized with polylysine-CB5) produced type specific opsonic antibodies as well (FIG. 4). It should be noted, however, that none of the CB5 immunized animals responded until after the first booster injection of polylysine conjugated CB5 in NaCl/P. Immunodiffusion tests in agar gels indicated that the antisera against each of the native and synthetic peptide fragments reacted in a precipitin line of identity with pep M24 and each of the albumin conjugated peptide fragments (FIG. 5). The failure of the unconjugated peptide fragments to precipitate with any of the immune sera indicated the haptenic properties of each of the peptides. These results indicate that each of the native and synthetic peptide fragments contain epitopes that are capable of evoking type specific opsonic antibodies against type 24 streptococci.

Similar results were obtained when the conjugates of the peptides were administered with MDP.

Because certain streptococcal M proteins contain epitopes that raise tissue cross-reactive antibodies (4), each of the immune rabbit sera was tested for cross-reactivity with human heart sarcolemmal membranes. None of the sera reacted in immuno-fluorescence tests with frozen sections of human heart tissue or with isolated sarcolemmal membranes. To obtain further proof that the CNBr peptide fragments lacked heart cross-reactive epitopes, each of the peptide fragments were used at concentrations of 250 M in tests of the inhibition of sarcolemmal immunofluorescence produced by an antiserum raised in a previous study (4) against type 5 streptococcal M protein. None of the peptide fragments was able to reduce the immunofluorescence reaction whereas type 5 protein (pep M5) tested at a concentration of 33 M completely blocked the reaction as previously described (4).

Figure 6:
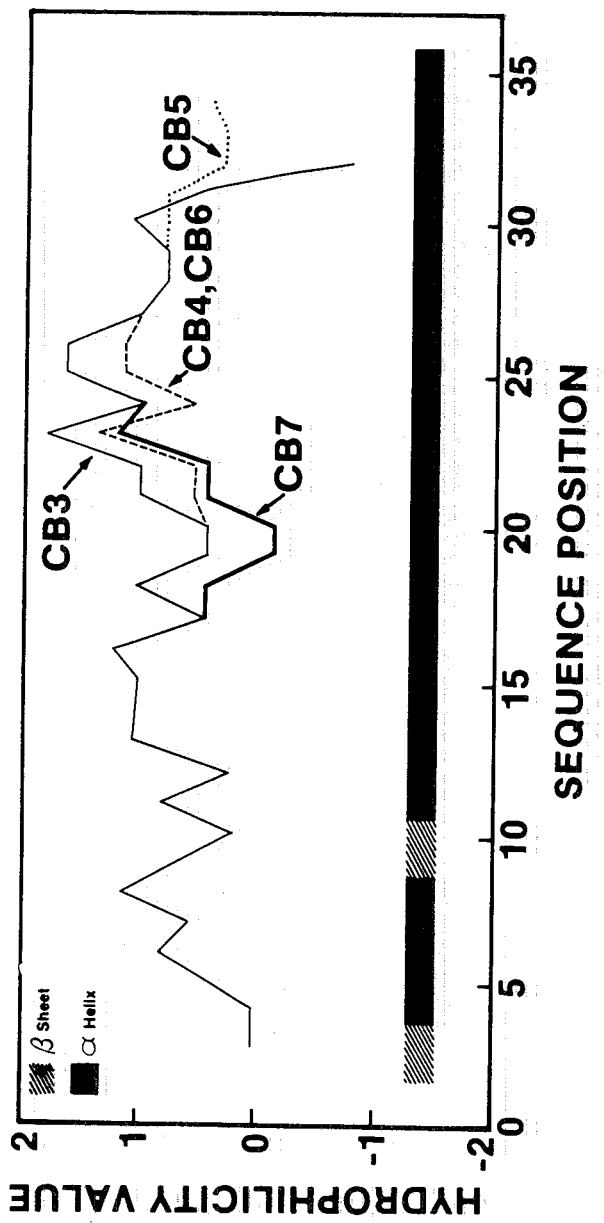
FIG. 6 shows hexapeptide hydrophilicity profiles and tertiary structural potentials of CB3, CB4, CB5, CB6, and CB7 of pep M24.

Since previous studies had indicated that the M24 molecule contains several distinct type specific protective antigens, the reactivities of each of the native CNBr peptides was examined with a set of protective and nonprotective monoclonal antibodies raised against the uncleaved pep M24 molecule (19). As can be seen in table III, each of the monoclonal antibodies gave a different pattern of reactivity with the seven CNBr peptides of pep M24. Interestingly, the monoclonal antibodies detected differences as small as one amino acid substitution. For example, the nonprotective antibody produced by clone IIB4.1 reacted strongly with CB4 but not at all with CB6 whereas the protective antibody in clone IIA6.8 reacted with CB6 but not with CB4. Yet, the two peptides differ by only one amino acid substitution at position 26 (see Table II). Furthermore, the Asp/Glu substitution at this position is conservative with respect to the relative hydrophilicity value of each of these amino acids (20). When analyzed for hexapeptide regions of hydrophilicity by the method of Hopp and Woods (20), CB4 and CB6 gave identical hydrophilicity profiles (FIG. 6). CB3, CB5, and CB7, on the other hand, each yield hydrophilicity profiles that are different from CB4 and CB6 (FIG. 6). It is possible, therefore, that some of the differences in reactivity with the monoclonal antibodies depend on differences in hydrophilicity. At least one marked difference in antigenicity (that between CB4 and CB6), however, cannot be explained on this basis.

Structural analyses of each of the complete covalent structures by the method of Chou and Fasman (21) indicates that the high degree of α-helical potential that had been reported previously (22) for the $NH_2$-terminal regions of these CNBr peptides is retained to the COOH-terminus of each peptide (FIG. 6). Peptide fragments CB3-7 all showed similar tertiary structural potentials and, therefore, the data obtained by these methods of analysis fail to account for differences in epitope specificity.

EXAMPLE 1

Isolation and Purification of M Protein

A polypeptide fragment of M portion was isolated and purified from limited peptic digests of whole cells of type 24 S. pyogenes as described (1, 5). The purified polypeptide (pep M24) was judged to be pure by sodium dodecyl sulfate-gel electrophoresis and amino acid analysis (1).

EXAMPLE 2

Cleavage with Cyanogen Bromide (CNBr)

Fifty-milligram samples of purified pep M24 were dissolved in 20 ml of 70% formic acid and digested under $N_2$ with CNBr at 40° C. for 4h. The digests were diluted wth 10 volumes of ice-cold distilled water and lyophilized. The CNBr peptides were separated and purified by gel filtration through columns of Sephadex G50SF (Pharmacia), followed by ion exchange chromatography at 43° C. on columns of carboxymethylcellulose (Whatman CM-52) as previously described (1).

EXAMPLE 3

Enzymatic Digestion of CNBr Peptides

Digestions with trypsin (TPCK-treated, three times crystallized, Worthington) were performed in 0.05M $NH_4HCO_3$, pH 8.3. An enzyme/substrate ratio of 1:50 (w/w) was used as described (6). The tryptic peptides of CB3, CB4, and CB5 were separated by automated peptide analysis on a column (0.9×24 cm) of PA-35 resin (Beckman) at 60° C. (7). Separation was achieved using a nine-chamber gradient mixer starting with 0.02M sodium citrate buffer, pH 3.8 and an automatic peptide analyzer (Technicon) equipped with a stream splitting device which permitted continuous monitoring of ninhydrin reactive peptides on 10% of the column effluent while collecting fractions of the remaining 90% of the effluent. The pH of each of the pooled fractions was adjusted to 2.0 with 1N HCl and the solutions were desalted on columns (1×2 cm) of Dowex 50-X8 (200 to 400 mesh, Bio-Rad) (8).

EXAMPLE 4

Chemical Synthesis of S-CB3

A polypeptide identical to native CB3 except that methionine was substituted for homoserine at the COOH-terminus was synthesized by solid phase techniques in an automated peptide synthesizer. The crude deblocked synthetic peptide was purified by HPLC on Ultrasphere ODS2 (Whatman).

EXAMPLE 5

Analytical Methods

Quantitative amino acid analyses were performed as described (9). Samples were hydrolyzed in doubly distilled, constantly boiling HCl under $N_2$ for 24 h at 108° C. The hydrolyzed samples were then analyzed with a Beckman 121 automatic amino acid analyzer by a single column technique using a four-buffer elution system (9). No corrections were made for the loss of labile amino acids (threonine, serine, methionine, and tyrosine) or the incomplete release of valine.

Automated Edman degradations were performed with a Beckman Sequenator (model 890C) according to the principles first described by Edman and Begg (10). The slow peptide-DMMA (071472) program of Beckman Instruments was used (11). The phenylthiohydantoins were identified by HPLC (12). Arginine derivatives were identified as their parent amino acids after hydrolysis with 55% HI (13). Repetitive yields of 97% were obtained during automated Edman degradation.

EXAMPLE 6

Conjugation of CB3, CB4, CB5 and S-CB3 with Polylysine

The native and synthetic peptides were conjugated to polylysine with carbodiimide (14). The conjugation Mixtures consisted of 15 nmol of polylysine ($Mr \approx 70,000$, Sigma), 75 nmol of CB3, CB4, CB5 or S-CB3 and 3 mg of cyanomide (carbodiimide; hydrogen cyanomide, Sigma) mixed in a total volume of 1.575 ml of distilled water. The mixtures were stirred for 18 h at 22° C., dialyzed for 24 h against distilled water, and for 6 h against 0.15M NaCl, and then stored frozen at −70° C.

EXAMPLE 7

Immunization of Rabbits

To determine the immunogenicity of CB3, CB4, CB5, and S-CB3, New Zealand White rabbits (2 kg) were injected subcutaneously with a 25 nmol dose of polylysine-conjugated peptide emulsified in complete Freund's adjuvant (2). Rabbits were bled immediately before the immunizing injection and at 2-week intervals thereafter. At six and ten weeks, each rabbit was injected subcutaneously with a 25 nmol booster doses of the respective conjugated peptide in 0.02M phosphate, 0.15M NaCl, pH 7.4 ($NaCl/P_i$) and sera were collected 2 weeks after each booster dose. Antisera against the uncleaved pep M24 molecule were prepared by similarly immunizing rabbits with 3 nmole doses of pep M24 (5). All sera were stored at 4° C.

EXAMPLE 8

Assays for M Antibody and M Antigens

The rabbit sera were assayed for the presence of anti-M protein antibodies by enzyme-linked immunosorbent assays (ELISA), immunoprecipitation tests in agar gels and opsonic antibody tests. ELISA was performed as previously described (15) except that pep M24 was adsorbed to the walls of plastic cuvettes and a semi-automatic analyzer and injector system (EIA PR50, Gilford) was used. ELISA titers are expressed as the reciprocal of the highest dilution of serum giving and absorption >0.1 at 405 nm. Immunoprecipitin tests were performed by double diffusion in agar gel as described (16).

Opsonic antibodies were assayed as described in detail elsewhere (1, 5). Briefly, the test mixtures consisted of 0.4 ml fresh heparinized (10 U ml$^{-1}$) human blood, 0.05 ml of a standard suspension of phagocytosis resistant streptococci and 0.05 ml of various dilutions of test serum. The ratio of streptococcal colony forming units (CFU) per leukocyte was approximately 10:1. The percentage of neutrophilic leukocytes counted that had ingested one or more bacteria was estimated by microscopic examination of stained smears prepared from a drop of test mixture after incubation for 30 min at 37° C. The opsonic antibody titers are expressed as the reciprocal of the highest twofold dilution of test serum in three separate tests that promoted phagocytosis of streptococci in ≧10% of the neutrophils counted after incubation at 37° C. for 30 min; the same organisms in the presence of premium rabbit serum were phagocytosed by ≦2% of neutrophils in each test. Antisera giving titers of >1:4 produced phagocytosis in the range of 40–70% when undiluted. The results of phagocytosis tests were confirmed by indirect bactericidal tests performed as previously described (17). The serotype specificity of the antibodies was determined by testing the capacity of the antisera to promote the phagocytosis of heterologous M serotypes of S. pyogenes.

EXAMPLE 9

ELISA and Opsonic Antibody Inhibition Tests

ELISA inhibition tests were performed by incubating a constant dilution of antiserum with serial dilutions of soluble polypeptide antigen in 0.25 ml NaCl/P$_i$ (15). The mixtures were incubated at 37° C. for 30 min and then added to the antigen coated ELISA cuvettes. The dilution of immune serum used in these inhibition assays was one that was known to give an absorbance reading of 0.6–0.8 at 405 nm in the absence of the inhibiting antigen.

Tests for the inhibition of type-specific opsonization of homologous M serotypes of S. Pyogenes were performed as described (1, 5). Samples of opsonic antisera diluted in NaCl/P$_i$ to the highest dilution that promoted phagocytosis of homologous type streptococci by 40–60% of the neutrophils in phagocytosis tests were incubated with serial dilutions of M protein or its derived native or synthetic peptides. After removing any immunoprecipitates that may have formed, the incubation mixtures were used to treat homologous type streptococci in opsonphagcytosis test as described (1, 5). Results are expressed as the minimal amount (nmol) of M protein or its derived peptide needed to inhibit opsonization and phagocytosis of homologous type streptococci by 50%. Control experiments demonstrated that the streptococci used in these tests were phagocytosed by less 5% of neutrophils in inhibition assay mixtures containing preimmune rabbit sera. The results of the opsonic inhibition tests were confirmed by indirect bactericidal tests performed as described (17). Type specificity of opsonic antibodies was assured by the failure of the antisera to opsonize heterologous M serotypes of streptococci.

EXAMPLE 10

Immunofluorescence Tests

Each of the rabbit anisera was tested for immunologic cross-reactivity with human heart sarcolemmal membranes as previously described in detail (4). Frozen sections of human heart tissue or sarcolemmal membrane sheaths prepared by the method of van de Rijn et al. (18) and dried and fixed on glass slides (5) were reacted with immune rabbit serum followed by fluorescein-labeled goat anti-rabbit IgG and then examined by fluorescence microscopy (5). In control experiments, preimmune sera were substituted for the immune sera.

EXAMPLE 11

Hybridoma Antibodies and Epitope Mapping

Monoclonal antibodies prepared as previously described were characterized in a previous study (19) as to their protective and nonprotective anti-streptococcal properties. Two protective (IIA6.8 and IIC4.6) and one nonprotective (IIB4.1) monocloncal antibodies were chosen to use in mapping studies. For mapping studies, ELISA cuvettes were coated as described above with pep M24. The appropriately diluted antibodies (see above) were preincubated with 10 nmol of one of the CNBr peptides for 30 min at 37° C. before adding to the ELISA cuvettes. The results were recorded as the percent inhibition of ELISA.

EXAMPLE 12

Tertiary Structural and Hydrophilicity Analyses

The hydrophilicity profiles of the CNBr peptides were determined according to the method of Hopp and Wood (20) and the tertiary structural analyses were performed by the method of Chou and Fasman (21). To facilitate analysis, both procedures (with the generous assistance of Drs. David Kingsbury and Carlo Mainardi) were encoded in a BASIC program and run in an Apple II computer.

Remarkable primary structural homologies within the streptococcal M protein molecule have been demonstrated. A 35-residue peptide, with as few as one and no more than six amino acid substitutions is repeated at least five times in the type 24M protein molecule. It should be noted that the pepsin extracted M protein (pep M24) used in the studies represents a polypeptide fragment of a considerably larger molecule (23). Phillips et al. (24) demonstrated that whereas a peptic extract of type 5M protein had a m.w. of ≃30,000 that of a phage-associated lysin-extracted type 5M protein had a m.w. of ≃60,000. Thus, the 35-residue peptide of type 24M protein may be repeated even more than five times in the intact M protein molecule.

Not only is there a recurrence of the 35-residue peptide, but each of the peptides themselves contains internal repeats. This is particularly striking in CB3 which contains an over-lapping repeat of nine residues. Thus, the nine residues from positions 13–21 are identical to those at positions 20–28 except for a substitution of aspartic acid at position 26 for alinine at position 18 (see FIG. 2). Not taking the overlap into account the repeats are seven residues long.

The seven-residue periodicity of the primary structure of the NH2-terminal regions of type 24 streptococcal M protein has been pointed out to resemble that of the α-tropomyosin molecule of muscle tissue (22). Analysis of the data now shows that a high degree of α-helical potential is retained to the COOH-terminal amino acid residue of each of the smaller CNBr peptides. Indeed, x-ray defraction, circular dichroism, and rotary shadowing analyses have confirmed the predicted α- helical coiled-coil conformation of isolated M protein molecules (24).

Although the M protein molecule and α-tropomyosin share certain primary and conformational structural similarities, attempts to show significant immunological cross-sections between these molecules have been unsuccessful (4, 25). The question as to whether or not these molecules share immunological cross-reactive epitopes is of particular interest in view of the recent findings that certain M protein epitopes evoke opsonic antibodies that cross-react with the sarcolemmal membranes of human heart tissue (4); α-tropomyosin is abundant in these membranes. In previous studies, however, the blockage of heart-reactivity of such antibodies with purified preparations of rabbit heart α-tropomyosin (4) was not achieved.

Using monoclonal antibodies in an attempt to map protective determinants, shows that a single amino acid substitution within the 35-residue repeating peptide markedly alters antigenic reactivity. Furhermore, the alteration in epitope specificity is brought about by a conservative Asp/Glu substitution at position 26 of CB4 and CB6, respectively. Since the substitution does not influence the hexapeptide hydrophilicity profile (20) nor the tertiary structural potential (21) of this region of the molecule, it is likely that the monoclonal antibodies are directed toward other primary structural determinants encompassing the region of the substitution. Since the approximate size of an antigenic epitope encompasses six amino acid residues of protein molecules (26, 27) the substitution at any given position may influence the epitope specificities of any overlapping haxapeptide that includes up to 5 additional amino acid residues to either side of the substitution. Therefore, assuming that the primary structural epitope size indeed is six, a single amino acid substitution theoretically may influence the antigenic specificities of up to six epitopes. This consideration is of interest since two of the monoclonal antibodies used to detect the substitution were shown in a previous study to be opsonic and protective against virulent type 24 streptococci whereas the other (IIB4.1) was neither opsonic nor protective even though it reacted in high titer against the purified pep M protein molecule by ELISA (19). Thus, a single Asp/Glu substitution at position 26 rendered the peptide unrecognizable by the protective antibodies but recognizable by a nonprotective one. These findings indicate that structural features other than hydrophilicity and tertiary structural potential may influence not only epitope specificity but also the protective function of a particular region of a bacterial virulence protein.

The observation that minor amino acid substitutions may result in major changes in antigen-antibody interaction was first reported by Laver et al. (28). They demonstrated that the affinity of the interaction of a monclonal antibody with type A influenza virus was reduced five orders of magnitude by a single Ser/Leu substitution in an antigenic epitope of the virus.

The different patterns of reactivity of monclonal antibodies with the CNBr peptides of type 24M protein confirm the multiplicity of protective and nonprotective epitopes within the M protein molecule (15, 19). These initial mapping studies hold promise that monoclonal antibodies will be useful in identifying protective as opposed to nonprotective or even host tissue cross-reactive antigenic determinants.

Because of the fear that streptococcal M protein vaccines may contain antigenic determinants that evoke rather than prevent rheumatic heart disease, much effort has been directed toward defining precisely those epitopes of the M protein molecule needed to elicit not only protective but also tissue cross-reactive immune responses. The data demonstrates the feasibility of isolating and even chemically synthesizing limited peptide regions of M protein that retain protective immunogenicity when covalently linked to a carrier. None of the antibodies raised against the native or synthetic subpeptides reacted with human heart sarcolemmal membranes. Thus, the isolation or chemical synthesis of selected protective epitopes that lack tissue cross-reactivity should permit the disposal of a large part of the M protein molecule that harbors potentially harmful epitopes. Conversely, identification and synthesis of those epitopes that cross-react with host tissue sheds light on the pathogenesis of rheumatic heart disease as well as on the autoimmune response to structurally defined bacterial antigens in general.

The data definitively show that the whole M protein molecule is not needed to evoke protective immunity against *S. pyogenes* infections. The finding is of special interest since some M protein molecules have been shown to possess immunodeterminants that evoke cross-reactive immune responses against heart sarcolemmal membranes (4). The identification and chemical synthesis of protective peptide fragments of the M protein molecule that lack tissue cross-reactive epitopes may provide safe and effective vaccines against *S. pyogenes* infections, in particular against the strains that give rise to rheumatic fever and rheumatic heart disease.

More than 60 distinct M streptococcal strains have been identified. Type 24 streptococcal M protein raises antibodies which are not serologically cross-reactive with tissue antigens of the human or of the host heart. A more prevalent and very toxic strain, type 5M causes rheumatic fever. Antibodies raised against type 5M are serologically cross-reactive with heart tissue antigens.

In accordance with the invention, a 20-residue peptide of type 5M protein has proved to be immunogenic when covalently linked, for instance, to tetanus toxoid. The synthetic type 5M protein S-pep M5 (1-20) elicited high titers of opsonic and ELISA antibodies in each of three rabbits immunized with the synthetic peptide linked to tetanus toxoid and emulsified in complete Freund's adjuvant. The covalent structure of S-pep M5 (1-20) is as follows: Ala-Val-Thr-Lys-Gly-Thr-Ile-Asn-Asp-Pro-Gln-Ala-AlaLys-Glu-Ala-Leu-Asp-Lys-Tyr.

Quite remarkably, none of the immune rabbit sera reacted with human heart tissue, indicating that this region of the Type 5M protein molecule is devoid of the tissue cross-reactive epitope. Thus, this aspect of the invention provides definitive evidence that it is possible to avoid tissue cross-reactive antigenic determinants by synthesis of the appropriate subpeptides of M protein as performed herein.

The invention also encompasses biologically active compositions comprising the antigen and an immunostimulant and wherein the antigen is administered with the immunostimulant. CFA is one such immunostimulant. Other natural and synthetic immunostimulants are well known in the art. The administration need not be concurrent; one may precede the other, in part or all of it. What is important is that the two components are present in the system of the mammal concurrently.

The biological compositions of the invention can be in any suitable form for administration to the mammal, whether a human or animal. Such as known in the art.

Solid compositions for oral administration include compressed tablets, pills, powders and granules. In such solid compositions, at least one of the active ingredients is admixed with at least one inert diluent such as starch, calcium carbonate, sucrose or lactose. These compositions may also contain additional substances other than inert diluents, e.g. lubricating agents, such as magnesium stearate, talc and the like.

Liquid compositions for oral administration include pharmaceutically-acceptable emulsions, solutions, suspensions, syrups and elixirs containing inert dilutents commonly used in the art, such as water. According to the invention, the compounds for oral administration also include capsules of absorbable material, such as gelatin, containing said active component with or without the addition of diluents or excipients.

Preparations according to the invention for parenteral administration include sterile aqueous-organic, and organic solutions, suspensions and emulsions. Examples of organic solvents or suspending media are propylene glycol, polyethylene glycol, vegetable oils, such as olive oil, and injectable organic esters, such as ethyl oleate. These compositions can also contain adjuvants such as stabilising, preserving, wetting, emulsifying and dispersing agents. Aqueous compositions are by far preferred.

The percentages of active component in the said composition and method for causing the desired biological effect, (e.g. immunological or hormonal inhibitory) can be varied so that a suitable dosage is obtained. The dosage administered to a particular patient is variable, depending upon the clinician's judgment using as the criteria: The route of administration, the duration of treatment, the size and condition of the patient, the potency of the active component and the patient's response thereto. An effective dosage amount of active component can thus be determined best by the clinician considering all criteria and utilizing the best judgment on the patient's behalf. For practical considerations, the proportion may vary from about 0.01 to 20%, or higher, of active ingredient per composition. What is needed is that at least the minimum effective amount to give the desired effect be present.

Other aspects of the invention will readily become apparent to one skilled in the art.

References

1. Beachey, E. H., Seyer, J. M. & Kang, A. H. (1978) Proc. Natl. Acad. Sci. U.S.A. 75, 3163–3167.
2. Beachey, E. H., Seyer, J. M. & Kang, A. H. (1980) J. Biol. Chem. 255, 6284–6289.
3. Beachey, E. H., Seyer, J. M., Dale, J. B., Simpson, W. A. & Kang, A. H. (1981) Nature 292, 457–459.
4. Dale, J. B. & Beachey, E. H. (1982) J. Exp. Med. 156, 1165–1176.
5. Beachey, E. H., Stollerman, G. H., Chiang, E. Y., Chiang, T. M., Seyer, J. M. & Kang, A. H. (1977) J. Exp. Med. 145, 1469–1483.
6. Seyer, J. M. & Kang, A. H. (1977) Biochemistry 16, 1158–1164.
7. Kang, A. H. & Gross, J. (1970) Biochemistry 9, 796–804.
8. Hirs, C. H. W. (1967) Methods Enzymol. 11, 386–390.
9. Kang, A. H. (1977) Biochemistry 11, 1828–1835.
10. Edman, P. & Begg, G. (1967) Eur. J. Biochem. 1, 80–91.
11. Dixit, S. N., Seyer, J. M., Oronsky, A. O., Corbett, C., Kang, A. H. & Gross, J. (1975) Biochemistry 14, 1933–1938.
12. Zimmerman, C. L., Pisano, J. J. & Appella, E. (1973) Biochem. Biophys. Res. Commun. 55, 1220–1224.
13. Smithies, O., Gibson, D., Fanning, E. M., Goodfleisch, R. M., Gilman, J. D. & Ballantyne, D. L. (1971) Biochemistry 10, 4912–2921.
14. Nisonoff, A. (1977) Methods Immunol. Immunochem. 1, 120–187.
15. Dale, J. B., Ofek, I. & Beachey, E. H. (1980) J. Exp. Med. 151, 1026–1037.
16. Munoz, J. (1970) Methods Immunol. Immunochem. 3, 146–160.
17. Beachey, E. H. & Stollerman, G. H. (1971) J. Exp. Med. 134, 351–365.
18. van de Rijn, I., Zabriskie, J. & McCarty, M. (1977) J. Exp. Med. 146, 479–487.
19. Hasty, D. L., Beachey, E. H., Simpson, W. A. & Dale, J. B. (1982) J. Exp. Med. 155, 1010–1018.
20. Hopp, T. P. & Wood, K. R. (1981) Proc. Natl. Acad. Sci. U.S.A. 78, 3824–3826.
21. Chou, P. Y. & Fasman, G. D. (1974) Biochemistry 13, 22–245.
22. Manjula, B. N. & Fischetti, V. A. (1980) J. Exp. Med. 151, 695–708.
23. van de Rijn, I. & Fischetti, V. A. (1981) Infect. Immun. 32, 86–91.
24. Phillips, G. N., Jr., Flicker, P. F., Cohen, C., Manjula, B. N. & Fischetti, V. A. (1981) Proc. Natl. Acad. Sci. U.S.A. 78, 4689–4693.
25. Beachey, E. H. & Seyer, J. M. (1982) in J. B. Robbins, J. C. Hill, & J. C. Sadoff (eds.), Seminars in Infectious Disease-Bacterial Vaccines, George Theime Verlag, New York 4, 401–410.
26. Atassi, M. Z. (1975) Immunochemistry 12, 423–438.
27. Kabat, E. A. (1968) Structural Concepts in Immunology and Immunochemistry (Holt, Rhinehart & Winsteon, New York) pp 89–100.
28. Laver, W. G., Gerhard, M., Webster, R. G., Frankel, M. E. & Air G. M. (1979) Proc. Natl. Acad. Sci. U.S.A. 76, 1425–1429.

TABLE I

| | Amino Acid Composition of Tryptic Peptides of CB3, CB4, and CB5 from Pep M24 | | | | | | | | | | | | |
|---|---|---|---|---|---|---|---|---|---|---|---|---|---|
| Amino acid | T1[a](CB3, CB4)[b] | T2(CB3)[b] | T2(CB4)[b] | T2-1(CB5)[b] | T3 | T4 | T5(CB3)[b] | T6(CB4)[b] | T5(CB5)[b] | T6 | CB3 | CB4 | CB5 |
| Aspartic acid | 0.3 | 0.8(1) | 1.2(1) | 3.2(3) | 2.4(2) | 0.2 | 0.3 | 0.2 | 0.2 | — | 3.3(3) | 3.2(3) | 5.3(5) |
| Threonine | — | 0.2 | 0.2 | 0.4 | 1.2(1) | 1.2(1) | — | — | — | — | 1.8(2) | 2.1(2) | 2.1(2) |
| Serine | — | — | 0.2 | 0.2 | 1.8(2) | 0.4 | — | — | — | — | 2.2(2) | 1.8(2) | 1.7(2) |
| Glutamic acid | 1.2(1) | 1.2(1) | 2.4(2) | 2.2(1) | 0.3 | 2.1(2) | 2.3(2) | 0.9(2) | 1.2(1) | — | 5.8(6) | 6.4(6) | 5.2(6) |
| Proline | — | — | — | — | — | — | — | — | — | — | — | — | — |
| Glycine | 1.0(1) | 0.2 | — | 1.4(1) | 0.2 | — | — | — | — | — | 1.0(1) | 1.0(1) | 1.0(1) |

TABLE I-continued

Amino Acid Composition of Tryptic Peptides of CB3, CB4, and CB5 from Pep M24

| Amino acid | T1[a](CB3, CB4)[b] | T2(CB3)[b] | T2(CB4)[b] | T2-1(CB5)[b] | T3 | T4 | T5(CB3)[b] | T6(CB4)[b] | T5(CB5)[b] | T6 | CB3 | CB4 | CB5 |
|---|---|---|---|---|---|---|---|---|---|---|---|---|---|
| Alanine | 2.1(2) | 1.0(1) | 1.2(1) | 3.4(3) | 1.8(2) | 1.0(1) | 2.8(3) | 3.2(3) | 2.9(3) | — | 9.3(9) | 8.8(9) | 9.2(9) |
| Valine | — | — | — | — | — | — | — | — | — | — | — | — | 0.3 |
| Iso-leucine | — | — | — | 0.2 | — | — | 0.2 | — | — | 0.9(1) | 0.7(1) | 0.6(1) | 0.8(1) |
| Leucine | 0.8(1) | 0.8(1) | 1.3(1) | 3.1(3) | — | 0.9(1) | 1.1(1) | 0.9(1) | 0.9(1) | — | 3.6(4) | 4.1(4) | 5.2(5) |
| Phenyl-alanine | — | — | — | — | 0.9(1) | — | — | — | — | — | 1.1(1) | 0.9(1) | 1.0(1) |
| Tyrosine | — | — | — | — | — | — | — | — | — | — | — | — | — |
| Histidine | — | — | — | — | — | — | — | — | — | — | — | — | 0.3 |
| Lysine | — | 1.2(1) | 0.8(1) | 1.3(1) | 0.9(1) | 1.1(1) | 0.8(1) | — | — | 1.0(1) | 5.2(5) | 4.1(4) | 4.4(4) |
| Arginine | — | — | — | 0.2 | — | — | — | 1.0(1) | 0.9(1) | — | 0.3 | 1.0(1) | 1.1(1) |
| Homo-serine[c] | 0.7(1) | — | — | 0.7(1) | — | — | — | — | — | — | 0.9(1) | 0.8(1) | 0.3(1) |
| Totals | 6 | 5 | 6 | 14 | 9 | 6 | 7 | 6 | 6 | 2 | 35 | 35 | 37 |

Values expressed as residues per peptide and given to the nearest 0.1 residue. —, indicates less than 0.1 residue present. Assumed integral values are given in parentheses.

TABLE II

Sequence of variable regions of CNBr peptides of pep M24

| Residue | CB3 | CB4 | CB5 | CB6[a] | CB7[a] |
|---|---|---|---|---|---|
| 21 | Glu | Glu | Glu | Glu | [Ala][b] |
| 22 | Ala | Ala | Ala | Ala | Ala |
| 23 | [Glu] | Arg | Arg | Arg | Arg |
| 24 | Lys | [Gln] | Lys | [Gln] | Lys |
| 25 | Ala | Ala | Ala | Ala | Ala |
| 26 | Asp | Asp | Asp | [Glu] | Asp |
| 27 | Leu | Leu | Leu | Leu | Leu |
| 28 | Glu | Glu | [Asp] | Glu | Glu |
| 29 | Lys | Lys | [Asp] | Lys | Lys |
| 30 | Ala | Ala | Ala | Ala | Ala |
| 31 | Leu | Leu | Leu | Leu | Leu |
| 32 | Glu | Glu | Glu | Glu | Glu |
| 33 | Gly | Gly | [Leu] | Gly | Gly |
| 34 | Ala | Ala | [Glu] | Ala | Ala |
| 35 | Hse | Hse | [Gly] | Hse | Hse |
| 36 | | | Ala | | |
| 37 | | | Hse | | |

[a]The previously reported (2) amino acid sequences of CB6 and CB7 are shown for comparison.
[b]Amino acid residues that are different or in the minority (i.e., position 24) at any position are enclosed in boxes.

TABLE III

Reactivities of monoclonal antibodies with CNBr peptides of pep M24 protein[a]

| Monoclonal antibody | Inhibition[b] of ELISA against pep M24 by: | | | | | | | pep M24 |
|---|---|---|---|---|---|---|---|---|
| | CB1 | CB2 | CB3 | CB4 | CB5 | CB6 | CB7 | |
| IIC4.6 | ++++ | ++++ | — | — | — | ++++ | ++++ | ++++ |
| IIA6.8 | ++++ | ++++ | ++++ | — | ++ | ++ | ++ | ++++ |
| IIB4.1 | ++ | + | ++ | +++ | + | — | +++ | ++++ |

[a]Each of these monoclonals antibodies has been characterized as to protective function in a previous study (19). The antibodies produced by clones IIC4.6 and IIA6.8 both were shown to be opsonic and promote killing of type 24 streptococci whereas the antibody produced by clone IIB4.1 was devoid of opsonic activity although it gave a high titer of reactivity by ELISA with the isolated pep M24 M protein molecult (19).
[b]The inhibition of ELISA was performed as described in "Methods" by adding 10 nmol of the respective antigen to the appropriate dilution of ascites fluid containing the monoclonal antibody. After incubation for 30 min at 37° C., the preincubated antibody was added to cuvettes coated with pep M24 as the solid phase antigen. The results of inhibition are recorded as relative inhibition of the ELISA by 10 nmol of the respective antigens: ++++, 80%; ++, 40–60%; +, 20–40%; —, 20% inhibition.

TABLE IV

| Yields of PTH-Amino Acid Derivatives (nmoles) Obtained After | | | | | | |
|---|---|---|---|---|---|---|
| Peptide Degraded Nanomoles Used | CB3 250 nmoles | T1 (CB3) 100 nmoles | CB4 200 nmoles | T1 (CB5) 100 nmoles | CB5 300 nmoles | T2-1 (CB5) 100 nmoles |
| Residue # | | | | | | |
| 1 | 160 | 43 | 98 | 74 | 210 | 43 |
| 2 | 173 | 62 | 163 | 59 | 238 | 61 |
| 3 | 18 | 31 | 12 | 43 | 22 | 53 |
| 4 | 78 | 24 | 94 | 40 | 68 | 40 |
| 5 | 153 | 25 | 149 | 29 | 193 | 32 |
| 6 | 147 | 12 | 152 | 9 | 195 | 44 |
| 7 | 23 | | 18 | | 16 | 37 |
| 8 | 140 | | 129 | | 188 | 28 |
| 9 | 132 | | 120 | | 170 | 16 |
| 10 | 136 | | 122 | | 178 | 21 |
| 11 | 139 | | 116 | | 182 | 19 |
| 12 | 106 | | 83 | | 132 | 14 |
| 13 | 95 | | 104 | | 154 | 8 |

TABLE IV-continued

| | Yields of PTH-Amino Acid Derivatives (nmoles) Obtained After | | | | | |
|---|---|---|---|---|---|---|
| Peptide Degraded Nanomoles Used | CB3 250 nmoles | T1 (CB3) 100 nmoles | CB4 200 nmoles | T1 (CB5) 100 nmoles | CB5 300 nmoles | T2-1 (CB5) 100 nmoles |
| 14 | 103 | | 95 | | 142 | |
| 15 | 117 | | 98 | | 133 | |
| 16 | 109 | | 84 | | 136 | |
| 17 | 69 | | 63 | | 121 | |
| 18 | 94 | | 78 | | 126 | |
| 19 | 103 | | 84 | | 139 | |
| 20 | 82 | | 51 | | 112 | |
| 21 | 82 | | 48 | | 98 | |
| 22 | 74 | | 48 | | 101 | |
| 23 | 70 | | 16 | | 79 | |
| 24 | 49 | | 8 | | 64 | |
| 25 | 56 | | 23 | | 66 | |
| 26 | 51 | | 19 | | 51 | |
| 27 | 40 | | 12 | | 42 | |
| 28 | 43 | | 10 | | 43 | |
| 29 | 22 | | 7 | | 49 | |
| 30 | 17 | | 9 | | 38 | |
| 31 | 6 | | 8 | | 34 | |
| 32 | | | | | 29 | |
| 33 | | | | | 33 | |
| 34 | | | | | 22 | |
| 35 | | | | | 8 | |

(1) Values expressed as nmole of phenylthiohydantoin amino acid or parent amino acid after HI hydrolysis.

I claim:

1. A synthetic antigen congugate which comprises a polyvalent linkable carrier covalently linked to a polypeptide which polypeptide comprises the amino acid sequence Asn-Phe-Ser-Thr-Ala-Asp-Ser-Ala-Lys-Ile-Lys-Thr-Leu-Glu-Ala-Glu-Lys-Ala-Ala-Leu-A-Ala-B-C-Ala-D-Leu-E-F-Ala-Leu-Glu-G-H-I wherein A is Glu or Ala
B is Glu or Arg
C is Lys or Gln
D is Asp or Glu
E is Glu or Asp
F is Lys or Asp
G is Gly or Leu
H is Ala or Glu
I is Hse, Met, Gly-Ala-Hse, or Gly-Ala-Met, with the proviso that the polypeptide is not any one of the four following sequences:

Asn-Phe-Ser-Thr-Ala-Asp-Ser-Ala-Lys-Ile-Lys-Thr-Leu-Glu-Ala-Glu-Lys-Ala-Ala-Leu-Ala-Ala-Arg-Lys-Ala-Asp-Leu-Glu-Lys-Ala-Leu-Glu-Gly-Ala-I, or

Asn-Phe-Ser-Thr-Ala-Asp-Ser-Ala-Lys-Ile-Lys-Thr-Leu-Glu-Ala-Glu-Lys-Ala-Ala-Leu-Glu-Ala-Arg-Gln-Ala-Glu-Leu-Glu-Lys-Ala-Leu-Glu-Gly-Ala-I, wherein I is Met or Hse, which antigen elicits type-specific opsonic antibodies to *Streptococcus pyogenes* and which is not serologically cross-reactive with tissue antigens of the heart.

2. The synthetic antigen of claim 1 wherein the polyvalent linked carrier is a natural protein carrier.

3. The synthetic antigen of claim 2 wherein the carrier is tetanus toxoid.

4. The synthetic antigen of claim 1 wherein the carrier is a synthetic polymer.

5. The synthetic antigen of claim 4 wherein the carrier is a polylysine.

6. An immunogenic biological composition which comprises a biologically acceptable diluent, an immunostimulant and in an amount sufficient to elicit opsonic antibodies to *Streptococcus pyogenes* and not be serologically cross-reactive with tissue antigens of the heart, a polypeptide having the amino acid sequence Asn-Phe-Ser-Thr-Ala-Asp-Ser-Ala-Lys-Ile-Lys-Thr-Leu-Glu-Ala-Glu-Lys-Ala-Ala-Leu-A-Ala-B-C-Ala-D-Leu-E-F-Ala-Leu-Glu-G-H-I wherein A is Glu or Ala
B is Glu or Arg
C is Lys or Gln
D is Asp or Glu
E is Glu or Asp
F is Lys or Asp
G is Gly or Leu
H is Ala or Glu
I is Hse, Met, Gly-Ala-Hse, or Gly-Ala-Met, with the proviso that the polypeptide is not any one of the four following sequences:

Asn-Phe-Ser-Thr-Ala-Asp-Ser-Ala-Lys-Ile-Lys-Thr-Leu-Glu-Ala-Glu-Lys-Ala-Ala-Leu-Ala-Ala-Arg-Lys-Ala-Asp-Leu-Glu-Lys-Ala-Leu-Glu-Gly-Ala-I, or

Asn-Phe-Ser-Thr-Ala-Asp-Ser-Ala-Lys-Ile-Lys-Thr-Leu-Glu-Ala-Glu-Lys-Ala-Ala-Leu-Glu-Ala-Arg-Gln-Ala-Glu-Leu-Glu-Lys-Ala-Leu-Glu-Gly-Ala-I, wherein I is Met or Hse.

7. An immunogenic biological composition which comprises a biologically acceptable diluent, an immunostimulant and in an amount sufficient to elicit opsonic antibodies to *Streptococcus pyogenes* and not be serologically cross-reactive with tissue antigens of the heart, the synthetic antigen of claim 1.

8. The immunogenic biological composition of claim 6 wherein the immunostimulant is complete Freund's adjuvant or a synthetic immunostimulant.

9. The immunogenic biological composition of claim 7 wherein the immunostimulant is complete Freund's adjuvant or a synthetic immunostimulant.

10. A method for controlling streptococcal infections in a mammal which comprises administering to a mammal in a dose sufficient to control *Streptococcus pyogenes*, the composition of claim 6, and controlling *Streptococcus pyogenes* in said mammal.

11. A method for controlling streptococcal infections in a mammal which comprises administering to a mammal in a dose sufficient to control *Streptococcus pyogenes,* the composition of claim 7 and controlling *Streptococcus pyogenes* in said mammal.

12. A method for controlling streptococcal infections in a mammal without causing cross-reactivity with heart tissue antigens which comprises administering to a mammal, in a dose sufficient to control *Streptococcus pyogenes,* the composition of claim 6, controlling *Streptococcus pyogenes* in said mammal without causing cross-reactivity with tissue antigens of the heart.

13. A method for controlling streptococcal infections in a mammal without causing cross-reactivity with heart tissue antigens which comprises administering to a mammal, in a dose sufficient to control *Streptococcus pyogenes,* the composition of claim 7, controlling *Streptococcus pyogenes* in said mammal without causing cross-reactivity with tissue antigens of the heart.

14. A synthetic antigen conjugate which comprises a polyvalent linkable carrier covalently linked to a polypeptide having the amino acid sequence Asn-Phe-Ser-Thr-Ala-Asp-Ser-Ala-Lys-Ile-Lys-Thr-Leu-Glu-Ala-Glu-Lys-Ala-Ala-Leu-Glu-Ala-B-C-Ala-Asp-Leu-E-F-Ala-Leu-Glu-G-H-I wherein B is Glu or Arg
C is Lys or Gln
D is Asp or Glu
E is Glu or Asp
F is Lys or Asp
G is Gly or Leu
H is Ala or Glu
I is Hse, Met, Gly-Ala-Hse, or Gly-Ala-Met, which antigen is able to elicit type-specific opsonic antibodies to *Streptococcus pyogenes* and which is not serologically cross-reactive with tissue antigens of the heart.

15. The synthetic antigen of claim 14 wherein the polyvalent linked carrier is a natural protein carrier.

16. The synthetic antigen of claim 14 wherein the carrier is a synthetic polymer.

17. The synthetic antigen of claim 14 wherein the carrier is polylysine.

18. An immunogenic biological composition which comprises a biologically acceptable diluent, an immunostimulant and in an amount sufficient to elicit opsonic antibodies to *Streptococcus pyogenes* and not be serologically cross-reactive with tissue antigens of the heart, the synthetic antigen of claim 14.

19. The immunogenic biological composition of claim 18 wherein the immunostimulant is complete Freund's adjuvant or a synthetic immunostimulant.

20. A method for controlling streptococcal infections in a mammal which comprises administering to a mammal in a dose sufficient to control *Streptococcus pyogenes,* the composition of claim 18, and controlling *Streptococcus pyogenes* in said mammal.

21. A method for controlling streptococcal infections in a mammal with causing cross-reactivity with heart tissue antigens which comprises administering to a mammal, in a dose sufficient to control *Streptococcus pyogenes,* the composition of claim 18 controlling *Streptococcus pyogenes* in said mammal without causing cross-reactivity with tissue antigens of the heart.

22. A synthetic antigen conjugate which comprises a polyvalent linkable carrier covalently linked to a polypeptide having the amino acid sequence Asn-Phe-Ser-Thr-Ala-Asp-Ser-Ala-Lys-Ile-Lys-Thr-Leu-Glu-Ala-Glu-Lys-Ala-Ala-Leu-Glu-Ala-Glu-Lys-Ala-Asp-Leu-Glu-Lys-Ala-Leu-Glu-Gly-Ala-Hse which antigen is able to elicit type-specific opsonic antibodies to *Streptococcus pyogenes* and which is not serologically cross-reactive with tissue antigens of the heart.

23. The synthetic antigen of claim 22 wherein the polyvalent linked carrier is a natural protein carrier.

24. The synthetic antigen of claim 22 wherein the carrier is a synthetic polymer.

25. The synthetic antigen of claim 24 wherein the carrier is polylysine.

26. An immunogenic biological composition which comprises a biologically acceptable diluent, an immunostimulant and in an amount sufficient to elicit opsonic antibodies to *Streptococcus pyogenes* and not be serologically cross-reactive with tissue antigens of the heart, the synthetic antigen of claim 22.

27. The immunogenic biological compositions of claim 26 wherein the immunostimulant is complete Freund's adjuvant or a synthetic immunostimulant.

28. A method for controlling streptococcal infections in a mammal which comprises administering to a mammal in a dose sufficient to control *Streptococcus pyogenes,* the composition of claim 26, and controlling *Streptococcus pyogenes* in said mammal.

29. A method for controlling streptococcal infections in a mammal without causing cross-reactivity with heart tissue antigens which comprises administering to a mammal, in a dose sufficient to control *Streptococcus pyogenes,* the composition of claim 18 controlling *Streptococcus pyogenes* in said mammal without causing cross-reactivity with tissue antigens of the heart.

30. A synthetic antigen conjugate which comprises a polyvalent linkable carrier covalently linked to the polypeptide having the amino acid sequence Asn-Phe-Ser-Thr-Ala-Asp-Ser-Ala-Lys-Ile-Lys-Thr-Leu-Glu-Ala-Glu-Lys-Ala-Ala-Leu-Glu-Ala-Arg-Gln-Ala-Asp-Leu-Glu-Lys-Ala-Leu-Glu-Gly-Ala-Hse which antigen is able to elicit type-specific opsonic antibodies to *Streptococcus pyogenes* and which is not serologically cross-reactive with tissue antigens of the heart.

31. The synthetic antigen of claim 30 wherein the polyvalent linked carrier is a natural protein carrier.

32. The synthetic antigen of claim 30 wherein the carrier is a synthetic polymer.

33. The synthetic antigen of claim 32 wherein the carrier is polylysine.

34. An immunogenic biological composition which comprises a biologically acceptable diluent, an immunostimulant and in an amount sufficient to elicit opsonic antibodies to *Streptococcus pyogenes* and not be serologically cross-reactive with tissue antigens of the heart, the synthetic antigen of claim 30.

35. The immunogenic biological composition of claim 34 wherein the immunostimulant is complete Freund's adjuvant or a synthetic immunostimulant.

36. A method for controlling streptococcal infections in a mammal which comprises administering to a mammal in a dose sufficient to control *Streptococcus pyogenes,* the composition of claim 34, and controlling *Streptococcus pyogenes* in said mammal.

37. A method for controlling streptococcal infections in a mammal without causing cross-reactivity with heart tissue antigens which comprise administering to a mammal, in a dose sufficient to control *Streptococcus pyogenes*, the composition of claim 34 controlling *Streptococcus pyogenes* in said mammal without causing cross-reactivity with tissue antigens of the heart.

38. A synthetic antigen conjugate which comprises a polyvalent linkable carrier covalently linked to a polypeptide having the amino acid sequence Asn-Phe-Ser-Thr-Ala-Ser-Ala-Lys-Ile-Lys-Thr-Leu-Glu-Ala-Glu-Lys-Ala-Ala-Leu-Glu-Ala-Arg-Lys-Ala-Asp-Leu-Asp-Asp-Ala-Leu-Glu-Leu-Glu-Ala-Hse which antigen is able to elicit type-specific opsonic antibodies to *Streptococcus pyogenes* and which is not serologically cross-reactive with tissue antigens of the heart.

39. The synthetic antigen of claim 38 wherein the polyvalent linked carrier is a natural protein carrier.

40. The synthetic antigen of claim 38 wherein the carrier is a synthetic polymer.

41. The synthetic antigen of claim 32 wherein the carrier is polylysine.

42. An immunogenic biological composition which comprises a biologically acceptable diluent, an immunostimulant and in an amount sufficient to elicit opsonic antibodies to *Streptococcus pyogenes* and not be serologically cross-reactive with tissue antigens of the heart, the synthetic antigen of claim 38.

43. The immunogenic biological composition of claim 34 wherein the immunostimulant is complete Freund's adjuvant or a synthetic immunostimulant.

44. A method for controlling streptococcal infections in a mammal which comprises administering to a mammal in a dose sufficient to control *Streptococcus pyogenes*, the composition of claim 42, and controlling *Streptococcus pyogenes* in said mammal.

45. A method for controlling streptococcal infections in a mammal without causing cross-reactivity with heart tissue antigens which comprises administering to a mammal, in a dose sufficient to control *Streptococcus pyogenes*, the composition of claim 42 controlling *Streptococcus pyogenes* in said mammal without causing cross-reactivity with tissue antigens of the heart.

46. A synthetic antigen conjugate which comprises a polyvalent linkable carrier covalently linked to a polypeptide having the amino acid sequence Asn-Phe-Ser-Thr-Ala-Asp-Ser-Ala-Lys-Ile-Lys-Thr-Leu-Glu-Ala-Glu-Lys-Ala-Ala-Leu-Glu-Ala-Gln-Lys-Ala-Asp-Leu-Glu-Lys-Ala-Leu-Glu-Gly-Ala-Met which antigen is able to elicit type-specific opsonic antibodies to *Streptococcus pyogenes* and which is not serologically cross-reactive with tissue antigens of the heart.

47. The synthetic antigen of claim 14 wherein the polyvalent linked carrier is a natural protein carrier.

48. The synthetic antigen of claim 46 wherein the carrier is a synthetic polymer.

49. The synthetic antigen of claim 48 wherein the carrier is polylysine.

50. An immunogenic biological composition which comprises a biologically acceptable diluent, an immunostimulant and in an amount sufficient to elicit opsonic antibodies to *Streptococcus pyogenes* and not be serologically cross-reactive with tissue antigens of the heart, the synthetic antigen of claim 46.

51. The immunogenic biological composition of claim 50 wherein the immunostimulant is complete Freund's adjuvant or a synthetic immunostimulant.

52. A method for controlling streptococcal infections in a mammal which comprises administering to a mammal in a dose sufficient to control *Streptococcus pyogenes*, the composition of claim 50, and controlling *Streptococcus pyogenes* in said mammal.

53. A method for controlling streptococcal infections in a mammal with causing cross-reactivity with heart tissue antigens which comprises administering to a mammal, in a dose sufficient to control *Streptococcus pyogenes*, the composition of claim 42 controlling *Streptococcus pyogenes* in said mammal without causing cross-reactivity with tissue antigens of the heart.

54. A synthetic antigen conjugate which comprises a polyvalent linkable carrier covalently linked to a polypeptide having the amino acid sequence Ala-Val-Thr-Lys-Gly-Thr-Ile-Asn-Asp-Pro-Gln-Ala-Ala-Lys-Glu-Ala-Leu-Asp-Lsy-Tyr which antigen is able to elicit type-specific opsonic antibodies to *Streptococcus pyogenes and which is not serologically cross-reactive with tissue antigens of the heart.*

55. An immunogenic biological composition which comprises a biologically acceptable diluent, an immunostimulant and in an amount sufficient to elicit opsonic antibodies to *Streptococcus pyogenes* and not be serologically cross-reactive with tissue antigens of the heart, the synthetic antigen of claim 54.

56. A method for controlling streptococcal infections in a mammal which comprises administering to a mammal in a dose sufficient to control *Streptococcus pyogenes*, the composition of claim 55, and controlling *Streptococcus pyogenes* in said mammal.

* * * * *